United States Patent [19]
Morneau

[11] Patent Number: 5,139,015
[45] Date of Patent: Aug. 18, 1992

[54] KNEE SUPPORT WRAP FOR LIFTING WEIGHTS

[76] Inventor: Kevin Morneau, 509-825 Granville St., V6Z 1K9 Vancouver, B.C., Canada

[21] Appl. No.: 780,007

[22] Filed: Oct. 21, 1991

[51] Int. Cl.$^5$ .................. A61F 13/00; A61F 5/37
[52] U.S. Cl. ........................... 602/62; 128/882
[58] Field of Search ............ 128/882, 892, 165, 80 R, 128/80 C, 80 F, 80 G, 157, 78, 87 A, 87 R, DIG. 15

[56] References Cited

U.S. PATENT DOCUMENTS

| | | | |
|---|---|---|---|
| 2,270,685 | 1/1942 | Miller | 128/165 |
| 3,373,741 | 3/1968 | Hill | 128/157 |
| 3,458,867 | 8/1969 | Moore | 128/165 |
| 3,480,012 | 11/1969 | Smithers | 128/157 |
| 3,556,096 | 1/1971 | Fuller | 128/157 |
| 4,084,586 | 4/1978 | Hettick | 128/165 |
| 4,296,744 | 10/1981 | Palumbo | 128/165 |
| 4,342,185 | 8/1982 | Pellen | 128/80 R |
| 4,370,978 | 2/1983 | Palumbo | 128/165 |
| 4,748,975 | 6/1988 | Yashima | 128/157 |
| 4,777,946 | 10/1988 | Watanabe | 128/882 |

Primary Examiner—Robert A. Hafer
Assistant Examiner—Michael Brown

[57] ABSTRACT

This invention relates to knee-support apparatus and to weightlifting accessories, and in particular discloses a support wrap for a weightlifter's knee. The wrap provides elastic support over the entire front and side portions of the knee while enabling easy attachment and detachment from the user's leg. The wrap also provides extra padded support over the periphery of the knee cap to prevent dislocation of the knee cap when the user is lifting heavy loads.

6 Claims, 2 Drawing Sheets

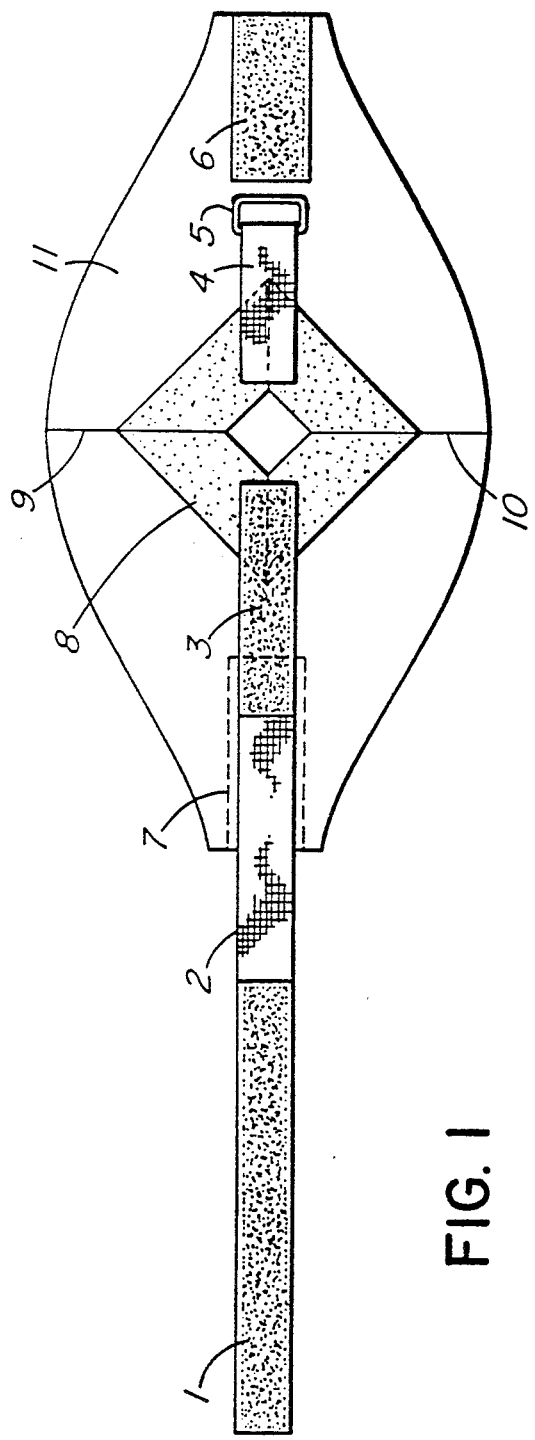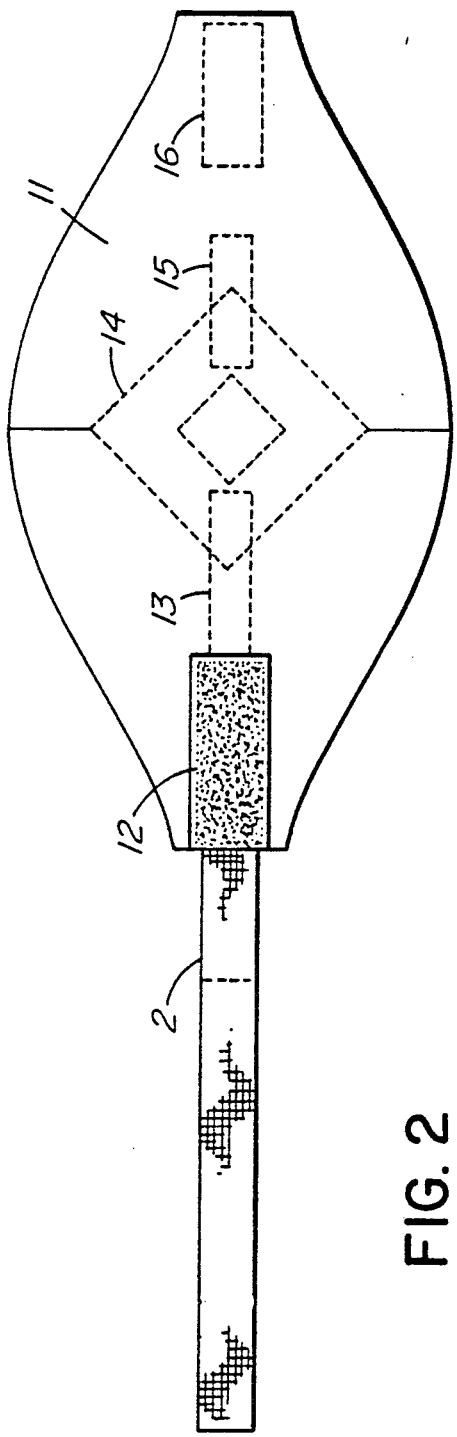

KNEE SUPPORT WRAP FOR LIFTING WEIGHTS

FIELD OF THE INVENTION

This invention relates to knee support apparatus and to weightlifting accessories, and in particular discloses an easily attachable and detachable knee support wrap having overall elastic support and extra padded support in the area to be worn around the periphery of the user's knee cap.

DESCRIPTION OF THE PRIOR TECHNOLOGY

The prior technology in this area consists essentially of tensor bandages, which provide some elastic support for a joint around which they are wrapped, but which are not easy to attach or detach, and which provide limited support that is undifferentiated with respect to the variety of body tissue at different places under the wrap.

SUMMARY AND OBJECTS OF THE INVENTION

The present invention is a weightlifter's knee support wrap, comprising a main layer of resilient material having an inherently cupped form, reinforcing padded means for covering an area surrounding a patulla bone on a knee of the weightlifter, the reinforcing padded means being affixed to a central surface area of the main layer, a strap affixed to a side area of the reinforcing padded means and extending across and affixed to an adjacent side area of the main layer and extending beyond the main layer, buckle means affixed to an opposite side area of the reinforcing padded means, a mechanically adhesive material patch affixed on a front surface side of the main layer and a complementary mechanically adhesive material patch affixed to a back surface opposite side of the main layer, in order that the wrap can be attached around a weightlifter's knee with a joining of the patches, the strap having a frontal mechanically adhesive material strip adjacent to the side area of the reinforcing padded means and a complementary frontal mechanically adhesive material strip on the strap beyond the main layer, in order that the strap can be passed through the buckle means and doubled back upon itself with a joining of the strips.

The main layer can be made of neoprene, which is resilient, elastic, and inherently padded. When stretched around a knee joint, it exerts considerable compressive tension. The reinforcing padded means gives extra support over the periphery of the patulla or knee cap, while not actually pressing excessively on the centre of the knee cap itself. This reduces or eliminating the possibility of the patulla being dislocated under the stress of a heavy lift.

The device can be given an inherently cupped form by cutting triangular sections from the top and bottom respectively of a piece of neoprene that is to form the main layer, and then gluing and stitching to top and bottom seams. The inherently cupped form adapts the main layer to fit around the knee, and in conjunction with the elasticity and resilience of the main layer, ensures a snug fit around the knee joint of the weightlifter.

DESCRIPTION OF THE DRAWINGS

FIG. 1 is a front view of the device.
FIG. 2 is a back view of the device.

DETAILED DESCRIPTION

Figure 4:
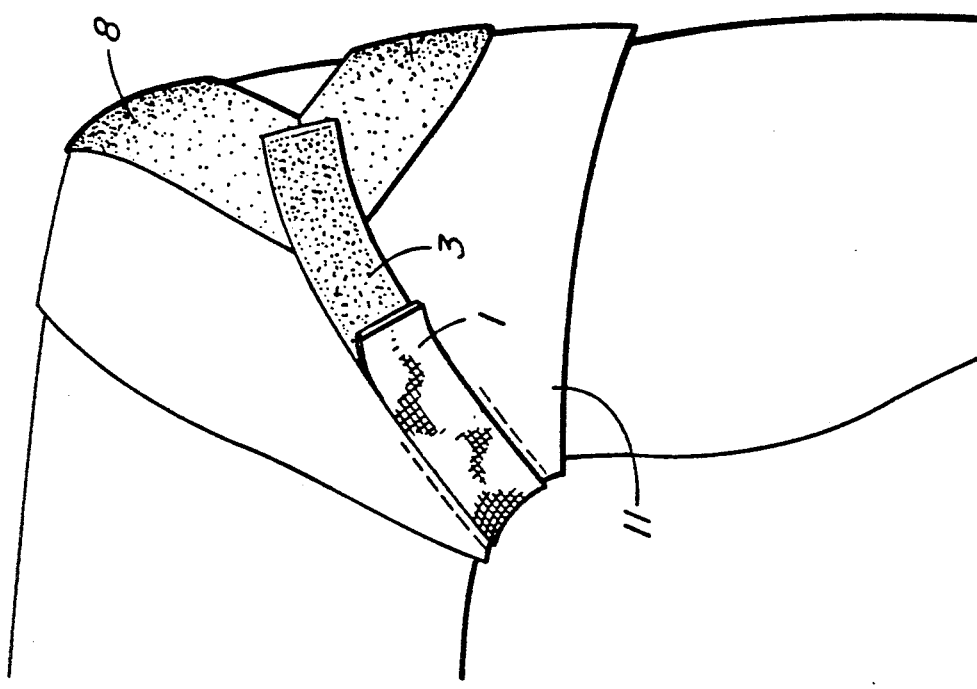
FIG. 4 is a perspective of the device wrapped about a weightlifter's knee.

Referring to FIG. 1, the strap 2 has a frontal mechancially adhesive material strip 3 and a complementary frontal mechancially adhesive material strip 1. The strap 2 is affixed to the reinforcing padded means 8 and extends over and is affixed to main layer 11. The buckle means comprises a strap section 4 sewn around a section of a buckle frame 5. The inherently cupped form of the wrap is obtained by a joining of a piece of the main layer material along top seam 9 and along bottom seam 10. The mechanically adhesive material patch 6 on the front side of the wrap is situated to be attached to the complementary mechanically adhesive material patch stitched at 7 on the back of the main layer 11.

Referring to FIG. 2, the complementary mechanically adhesive material patch 12 on the back of the main layer 11 is situated to be attached to the mechanically adhesive material patch stitched at 16 on the front side of the wrap. The stitching at 13, 14 and 15 affixes to the main layer 11 respectively the strap 2, the reinforcing padded means, and the buckle strap section.

Figure 3:
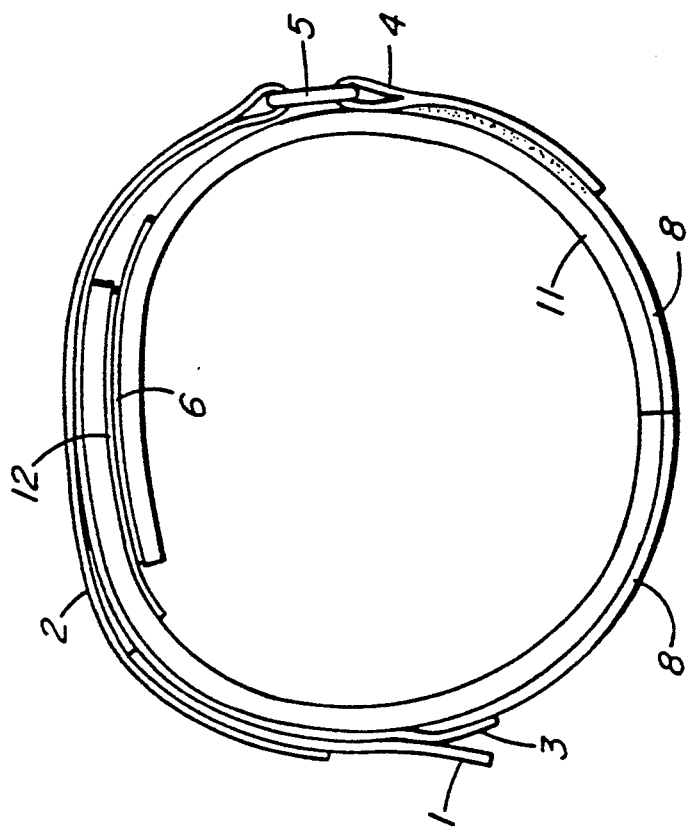
FIG. 3 is a top view of the device in its wrapped orientation.

Referring to FIG. 3, the frontal mechancially adhesive material strip 3 on the strap 2 is attached to the complementary frontal mechancially adhesive material strip 1, and the mechanically adhesive material patch 6 affixed on a front surface side of the main layer 11 is attached to the complementary mechanically adhesive material patch 12 affixed to a back surface opposite side of the main layer 11. The position of the patch 6 can be adjusted with respect to patch 12 to control the compressive tension of the main layer 11 when it is wrapped around the weightlifter's knee. The strap 2 has been doubled back upon itself after having been passed through buckle frame 5, one section of which is enclosed by strap section 4, which is in turn affixed to the reinforcing padded means 8. The top seam 9 is also shown.

Referring to FIG. 4, the end of the strap 2 can be grasped by the weightlifter and pulled to at different positions against the frontal mechanically adhesive strip 3 to adjust further the compressive tension of the reinforcing padded means 8 and of the wrap as a whole.

The wrap can be used in weight training, recreational weightlifting, and in any industrial or domestic activity involving the lifting of weights which might otherwise cause the knee ligaments to be strained or the knee joint bones to be dislocated.

The within-described invention may be embodied in other specific forms and with additional options and accessories without departing from the spirit or essential characteristics thereof. The presently disclosed embodiment is therefore to be considered in all respects as illustrative and not restrictive, the scope of the invention being indicated by the appended claims rather than by the foregoing description, and all changes which come within the meaning and range of equivalence of the claims are therefore intended to be embraced therein.

I claim:
1. A weightlifter's knee support wrap, comprising a main layer of resilient material having an inherently cupped form, reinforcing padded means for covering an area surrounding a patulla bone on a knee of the weigh- tlifter, the reinforcing padded means being affixed to a central surface area of the main layer, a strap affixed to a side area of the reinforcing padded means and extending across and affixed to an adjacent side area of the main layer and extending beyond the main layer, buckle means affixed to an opposite side area of the reinforcing padded means, a mechanically adhesive material patch affixed on a front surface side of the main layer and a complementary mechanically adhesive material patch affixed to a back surface opposite side of the main layer, in order that the wrap can be attached around a weightlifter's knee with a joining of the patches, the strap having a frontal mechanically adhesive material strip adjacent to the side area of the reinforcing padded means and a complementary frontal mechanically adhesive material strip on the strap beyond the main layer, in order that the strap can be passed through the buckle means and doubled back upon itself with a joining of the strips.

2. The device of claim 1, in which the main layer is made of neoprene.

3. The device of claim 2, in which the main layer has a pair of seams that give the main layer an inherently cupped form, the buckle means comprises a strap section sewn around a section of a buckle frame, and the reinforcing padded means frames an area in the centre of the main layer that is not covered by the reinforcing padded means.

4. The device of claim 1, in which the main layer has a pair of seams that give the main layer an inherently cupped form.

5. The device of claim 1, in which the buckle means comprises a strap section sewn around a section of a buckle frame.

6. The device of claim 1, in which the reinforcing padded means frames an area in the centre of the main layer that is not covered by the reinforcing padded means.

* * * * *